US006207193B1

(12) United States Patent
Pellegrini

(10) Patent No.: US 6,207,193 B1
(45) Date of Patent: Mar. 27, 2001

(54) TRANSDERMAL DRUG DELIVERY SYSTEM

(75) Inventor: Frank C. Pellegrini, Dix Hills, NY (US)

(73) Assignee: Stephen E. Feldman, New York, NY (US)

( * ) Notice: Subject to any disclaimer, the term of this patent is extended or adjusted under 35 U.S.C. 154(b) by 0 days.

(21) Appl. No.: 09/472,280

(22) Filed: Dec. 27, 1999

(51) Int. Cl.$^7$ ........................................... A61K 9/14
(52) U.S. Cl. ................ 424/486; 424/487; 424/489; 424/449; 424/484; 424/501
(58) Field of Search .................... 424/449, 489, 424/484, 501, 486, 487

(56) References Cited

U.S. PATENT DOCUMENTS

| | | | |
|---|---|---|---|
| 3,972,999 | 8/1976 | Tsuk . | |
| 4,329,332 | * 5/1982 | Couvreur et al. | 424/9 |
| 4,671,953 | * 6/1987 | Stanley et al. | 424/440 |
| 4,913,908 | * 4/1990 | Couvreur et al. | 424/501 |
| 5,356,635 | * 10/1994 | Raman et al. | 424/448 |
| 5,518,730 | * 5/1996 | Fuisz | 424/426 |
| 5,593,824 | 1/1997 | Treml et al. . | |

* cited by examiner

Primary Examiner—Thurman K. Page
Assistant Examiner—Isis Ghali
(74) Attorney, Agent, or Firm—Stephen E. Feldman, P.C.

(57) ABSTRACT

There is disclosed a transdermal drug delivery system wherein a drug or therapeutic agent is encapsulated in a water soluble carbohydrate. The carbohydrate-encapsulated drug or therapeutic agent, in the form of finely divided particles, is suspended in a cyanoacrylate ester which is applied to the skin of a mammal. Moisture on the skin and contact with skin tissue causes the cyanoacrylate to polymerize and the moisture on the skin also dissolves the carbohydrate permitting the drug or therapeutic agent, over time, to enter the body system through the pores of the skin.

43 Claims, No Drawings

TRANSDERMAL DRUG DELIVERY SYSTEM

FIELD OF THE INVENTION

This invention relates to a novel transdermal drug delivery system. More particularly, this invention relates to a drug delivery system capable of delivering a drug or therapeutic agent over time epidermally or transdermally through the skin of a human. Even more particularly, this invention relates to a time release, transdermal drug delivery system wherein the active drug or therapeutic agent is encapsulated in a carbohydrate matrix which is, in turn, suspended in a cyanacrylate ester.

BACKGROUND OF THE INVENTION

The use of carbohydrates as carriers for drugs or therapeutic agents is well known. For example, U.S. Pat. No. 3,972,999 to Tsuk discloses miscible melt mixes of amorphous griseofulvin and polyglycolides or lactic acid modified polyglycolides which are formed by heating together the crystalline griseofulvin and the polyglycolide until they melt and form a clear liquid. The liquid is then cooled and subdivided to be incorporated into dosage forms for administration as tablets, capsules, and the like.

U.S. Pat. No. 4,671,953 to Stanley, et. al. discloses a drug dispersed within a carbohydrate mass which is given to a patient to suck on enabling the drug to be released into the patient's mouth as the carbohydrate mass dissolves. The carbohydrates disclosed as useful include sucrose, sorbitol, mannitol or other sweeteners such as aspartanes.

U.S. Pat. No. 4,356,635 to Raman, et. al. discloses a sustained release composition for therapeutic agents formed from a biodegradable, amorphous carbohydrate glass matrix, a hydrophobic substance and a biologically active therapeutic agent. The composition is administered orally or is implanted in an animal where the amorphous carbohydrate glass matrix slowly degrades to release the therapeutic agent. The amorphous carbohydrate component is mixed with an agent to retard its recrystallization. The carbohydrate components that can be used are disaccharides such as sucrose, lactose, maltose or cellobiose and the retarding agents that can be used include polyvinylpyrrolidone, polyethylene glycols, polyvinyl alcohol, maltodextrins, sodium lauryl sulfate, oleyl alcohol, stearyl alcohol, and the like.

U.S. Pat. No. 4,593,824 to Treml, et. al. discloses a homogeneous solution of a glass forming filler material, a biological reagent and water having a viscosity enabling droplets thereof to be dispersed on an inert cryogenic surface and vacuum dried to form a spherical biological reagent that is stable at room temperature and soluble in water. The glass forming filler material is formed from a mixture of a high molecular weight synthetic carbohydrate polymer and a second carbohydrate. The synthetic carbohydrate polymer is used to provide structural integrity and the second carbohydrate is used to provide increased solubility. The high molecular weight synthetic carbohydrate polymer has a molecular weight of at least 10,000 and the second carbohydrate can be melezitose, cellobiose, DEXTRANTO resin, malotriose, maltose, cyclodextran, sorbitol, trehalose, PEG and sucrose.

The use of cyanoacrylates with drugs and therapeutic agents is also known. For example, U.S. Pat. Nos. 4,329,332 and 4,913,908, both to Couvreur, et. al., disclose submicroscopic particles formed from a polymerized alkyl cyanoacrylate containing a biologically active substance. In the '332 patent, the polymerized alkyl cyanoacrylates used contain 1–4 carbon atoms and the submicroscopic particles obtained can be dispensed orally, subcutaneously, intradermally, intramuscularly or intraveneously. The '908 patent discloses that the alkyl can be linear or branched and can contain 1–12 carbon atoms.

In U.S. Pat. No. 5,254,132 to Barley, et. al. there is disclosed cyanoacrylate adhesives which are used as an adjunct covering and closure material in combination with sutures or staples to close surgical openings.

U.S. Pat. No. 5,518,730 to Fuisz discloses obtaining a biodegradable controlled release composition formed by melt-spinning a non-saccharide biodegradable polymer and a bio-effecting agent. The polymers that can be used are any melt-spinnable thermoplastic polymers that are capable of being biodegraded in the body of an animal. The useful polymeric materials include poly(alkyl)cyanoacrylate.

In U.S. Pat. No. 5,753,699 to Greff, et. al. there is disclosed an antimicrobial cyanoacrylate composition which is applied to a non-saturable, superficial wound surface. The cyanoacrylate ester employed polymerizes in situ to form a film over the wound to promote wound healing and protect it against infection.

In U.S. Pat. No. 5,811,091 to Greff, et. al. there is disclosed cyanoacrylate compositions containing a compatible antimicrobial agent, particularly a compatible iodine-containing antimicrobial agent. The compositions polymerize in situ to form a protective antimicrobial polymeric film on mammalian skin.

As can be seen, the foregoing patents disclose various uses of carbohydrates and cyanoacrylates in connection with drug delivery systems or as antimicrobial protective films. None of these patents disclose, much less suggest, the combination of a carbohydrate-containing drug or therapeutic agent carried by a cyanoacrylate ester for use as a time release, transdermal drug delivery system.

BRIEF DESCRIPTION OF THE INVENTION

It has now been found that by encapsulating a drug or therapeutic agent in a carbohydrate and suspending the thusly encapsulated drug or therapeutic agent in a cyanoacrylate ester an effective, time release transdermal drug delivery system is obtained. When applied to the skin of a mammalian, moisture on the skin and skin tissue contact causes the cyanoacrylate ester to polymerize to form a protective coating or seal over the carbohydrate-encapsulated drug or therapeutic agent. Over time, moisture on the skin also dissolves the carbohydrate thereby releasing the drug or therapeutic agent and enabling the drug or therapeutic agent to contact the skin and enter the body system through the pores of the skin.

DETAILED DESCRIPTION OF THE INVENTION

In general, the transdermal drug delivery system of the invention comprises: a drug or therapeutic agent encapsulated in a carbohydrate, said carbohydrate-encapsulated drug or therapeutic agent being suspended in a cyanoacrylate ester.

The drugs or therapeutic agents that can be employed in the drug delivery system of the invention are those that are stable and retain their integrity at elevated temperatures and which are water soluble or are soluble in an aqueous medium. These drugs or therapeutic agents include antibiotics, antivirals, antifungals, antibacterials, analgesics, antiseptics, and the like.

Illustrative antibiotics that can be used are bacitracin, neomycin, chlorohexidine gluconate, erythromycin, polymyxin B and tetracylcine. An illustrative antiviral that can be used is acyclovir. Illustrative antifungals that can be used are ciclopirox, clotrimazole, gentian violet, oxiconazole and penticiclovir. Illustrative antibacterials that can be used are benzalkonium chloride, gentian violet and thimerosal.

Throughout the application and in the appended claims, it should be understood and is intended to be understood that use of the terms "drug", "drugs", therapeutic agent" and "therapeutic agents" are interchangeable expressions defining the same or similar entities.

The carbohydrates that can be used in the drug delivery system of the invention are also those that are water soluble or that are soluble in an aqueous medium such as monosaccharides and disaccharides.

Illustrative monosaccharides include those selected from the group consisting of glucose, mannose, galactose and fructose and illustrative disaccharides include those selected from the group consisting of sucrose, lactose, maltose and cellobiose.

The cyanoacrylate esters that can be employed in the drug delivery system of the invention are those that are capable of polymerizing upon contacting moisture. These cyanoacrylate esters have the general formula:

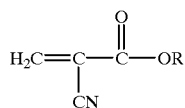

(Formula I)

wherein R is an alkyl of 2–12 C atoms, an alkenyl of 5–10 C atoms, phenyl, substituted phenyl, 2-ethoxyethyl and 3-methoxybutyl. Preferably R is a linear or branched alkyl of 2–10 C atoms such as ethyl, propyl, butyl, pentyl, hexyl, heptyl, octyl, nonyl and decyl and cyclic isomers thereof.

The transdermal drug delivery system of the invention can also include other components such as plasticizers to increase the flexibility of the cyanoacrylate ester containing the carbohydrate encapsulated drug as well as polymerization inhibitors to increase the stability of the cyanoacrylate ester and prolong its shelf life. A suitable plasticizer that can be used is dioctyl phthalate and a suitable polymerization inhibitor that can be used is sulfur dioxide.

Each of the components of the drug delivery system of the invention; i.e., the drug or therapeutic agent, the carbohydrate, the cyanoacrylate ester and, optionally, the plasticizer and polymerization inhibitor, are inert with respect to one another so that there is no interaction between them, even when they are exposed to moisture.

To prepare the drug delivery system of the invention, the drug or therapeutic agent is first dissolved or suspended in a molten carbohydrate. The carbohydrate is then permitted to cool and as it cools, it forms a glass-like matrix in which the drug or therapeutic agent becomes encapsulated. The carbohydrate matrix containing the drug or therapeutic agent is then pulverized into micro-fine sized particles which are then suspended in the cyanoacrylate ester.

The amount of drug or therapeutic agent that can be used to provide efficacy can be from about 5% to about 25% by weight of the carbohydrate employed, preferably from about 10–20% by weight.

The ratio of the carbohydrate-drug matrix to cyanoacrylate ester can be from about 1:2, preferably from about 1:5 by weight.

When employed in the transdermal drug delivery system, the plasticizer can be present in an amount of from about 5–20%, preferably 10–15% by weight, of the total composition and the polymerization inhibitor can be present in an amount of from about 20–400 ppm, preferably from about 50–300 ppm.

Prior to being suspended in the cyanoacrylate ester, the carbohydrate-drug matrix is pulverized or ground to a particle size having a diameter of from about 5–50 millimicrons (mmc), preferably from about 10–40 mmc.

To apply the drug delivery system of the invention, the cyanoacrylate ester containing the suspended carbohydrate-encapsulated drug or therapeutic agent is placed on the skin of a mammal such as a human. Upon contacting skin tissue and/or moisture on the skin, the cyanoacrylate ester polymerizes forming a thin film or coating that adheres to the body contours and provides a protective coating or seal for the carbohydrate-encapsulated drug or therapeutic agent. When the skin moisture contacts the water soluble carbohydrate, it dissolves releasing the drug or therapeutic agent enabling the drug or therapeutic agent to come into contact with the skin and enter the body through the pores of the skin. Since not all of the carbohydrate-encapsulated drug or therapeutic agent is contacted by the moisture of the skin and dissolved, the drug delivery system results in a time release of the drug or therapeutic agent into the body system.

The transdermal drug delivery system of the invention is further illustrated by the following examples.

EXAMPLE 1

To 100 mg. of molten glucose there can be added 10 mg. of penciclovir antiviral agent. The mixture can then be stirred to assure that all of the penciclovir is dissolved in the glucose. The molten glucose containing the penciclovir can then be allowed to cool to form a glass-like matrix. The cooled glass-like matrix can then be pulverized to obtain particles having a diameter of about 15 mmc. which can then be suspended in 400 mg. of a cyanoacrylate ester of Formula I where R is ethyl to obtain a transdermal drug delivery system of the invention.

EXAMPLE 2

Ten (10) mg. of bacitracin antibiotic agent can be dissolved in 50 mg. of molten sucrose which can then be permitted to cool to obtain a glass-like matrix. The cooled, glass-like matrix can then be ground to obtain particles having a diameter of about 5 mmc. and the particles can then be suspended in 100 mg. of a cyanoacrylate ester of Formula I where R is 2-ethoxyethyl to obtain a transdermal drug delivery system of the invention.

EXAMPLE 3

In 75 mg. of molten galactose there can be dissolved 7.5 mg. of neomycin antibiotic. The mixture can then be allowed to cool to obtain a glass-like matrix which can than be pulverized to obtain particulates having a diameter of about 25 mmc. The particles can then be suspended in 225 mg. of a cyanoacrylate ester of Formula I where R is butyl. To this suspension there can then be added 30 mg. of dioctyl phthalate as plasticizer to obtain a transdermal drug delivery system of the invention.

EXAMPLE 4

Thirty (30) mg. of erythromycin antibiotic can be dissolved in 150 mg. of molten lactose. The solution can then be permitted to cool to obtain a glass-like matrix which can then be pulverized to obtain particulates having a diameter of about 5 mmc. The particles can then be suspended in 150 mg. of a cyanoacrylate of Formula I where R is phenyl to obtain a transdermal drug delivery system of the invention.

EXAMPLE 5

In 100 mg. of molten mannose there can be dissolved 5 mg. polymyxin B antibiotic and the solution can be allowed to cool to form a glass-like matrix. The matrix can then be ground to obtain particles having a diameter of about 30 mmc. These particles can then be suspended in 200 mg. of a cyanoacrylate of Formula I where R is butyl. To this suspension there can then be added 200 ppm. of sulfur dioxide as polymerization inhibitor to provide a transdermal drug delivery system of the invention.

EXAMPLE 6

To 200 mg. of molten fructose there can be added 30 mg. of tetracycline antibiotic and the mixture can then be stirred to assure that all of the tetracycline is dissolved in the fructose. The molten fructose containing the tetracycline can then be permitted to cool to form a glass-like matrix. The cooled, glass-like matrix can then be pulverized to obtain particles having a diameter of about 20 mmc. These particles can then be suspended in 400 mg. of a cyanoacrylate of Formula I where R is 3-methoxybutyl to obtain a transdermal drug delivery system of the invention.

EXAMPLE 7

Five (5) mg. of benzalkonium chloride antibacterial can be dissolved in 50 mg. of molten maltose which can then be permitted to cool to form a glass-like matrix. The cooled, glass-like matrix can then be ground to obtain particles having a diameter of about 40 mmc. These particles can then be suspended in a cyanoacrylate ester of Formula I where R is pentyl. To this suspension there can then be added 10 mg. of dioctyl phthalate as plasticizer and 100 ppm. sulfur dioxide to obtain a transdermal drug delivery system of the invention.

EXAMPLE 8

In 100 mg, of molten cellobiose there can be dissolved 25 mg. of clotrimazole antifungal. This solution can then be permitted to cool to form a glass-like matrix. The glass-like matrix can then be ground to obtain particles having a diameter of about 10 mmc. These particles can then be suspended in 200 mg. of a cyanoacrylate ester of Formula I where R is octyl to obtain a transdermal drug delivery system of the invention.

Although the invention has been described in detail and with particularly it will be appreciated by those skilled in this art that changes and modifications can be made therein without departing from the scope an spirit of the invention encompassed in the claims.

What is claimed is:

1. A transdermal drug delivery system comprising:
   a drug or therapeutic agent encapsulated in a water soluble carbohydrate, said carbohydrate-encapsulated drug or therapeutic agent being suspended in a cyanoacrylate ester capable of polymerizing upon coming into contact with moisture or skin tissue.

2. The system of claim 1 wherein said carbohydrate-encapsulated drug or therapeutic agent is in the from of finely divided micro-fine particles.

3. The system of claim 1 wherein said drug or therapeutic agent is a member of the group consisting of antibiotics, antivirals, antifungals, antibacterials, analgesics and antiseptics.

4. The system of claim 2 wherein said particles have a diameter of from about 5 to about 50 millimicrons.

5. The system of claim 4 wherein said particles have a diameter of from about 10 to about 40 millimicrons.

6. The system of claim 1 wherein said carbohydrate is a monosaccharide or a disaccharide.

7. The system of claim 6 wherein said monosaccharide is a member of the group consisting of glucose, mannose, galactose and fructose.

8. The system of claim 6 wherein said disaccharide is a member of the group consisting of sucrose, lactose, maltose land cellobiose.

9. The system of claim 1 wherein said cyanoacrylate ester has the formula:

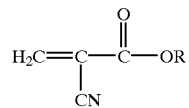

(Formula I)

wherein R is an alkyl of 2–12 C atoms, an alkenyl of 5–10 C atoms, phenyl, substituted phenyl, 2-ethoxyethyl, and 3-methyoxybutyl.

10. The system of claim 9 wherein R is a linear or branched alkyl of 2–10 C atoms and cyclic isomers thereof.

11. The system of claim 1 wherein said drug or therapeutic agent is present in an amount of from about 5 to about 26% by weight of said carbohydrate and the weight ratio of said carbohydrate-encapsulated drug or therapeutic agent to said cyanoacrylate ester is about 1:5.

12. The system of claim 11 wherein said drug or therapeutic agent is present in an amount of from about 10 to about 20% by weight of said carbohydrate and the weight ratio of said carbohydrate-encapsulated drug or therapeutic agent to said cyanoacrylate ester is about 2:4.

13. The system of claim 1 which can optionally include a plasticizer or a polymerization inhibitor.

14. The system of claim 13 wherein said plasticizer is dioctyl phthalate and said polymerization inhibitor is sulfur dioxide.

15. The system of claim 14 wherein said plasticizer is present in an amount of from about 5 to about 20% by weight and said polymerization inhibitor is present in an amount of from about 20 to about 400 ppm.

16. The system of claim 15 wherein said plasticizer is present in an amount of from about 10 to about 15% by weight and said polymerization inhibitor is present in an amount of from about 50 to about 300 ppm.

17. A transdermal drug delivery system comprising:
   a drug or therapeutic agent encapsulated in a water soluble carbohydrate, said carbohydrate-encapsulated drug or therapeutic agent being in the form of finely divided micro-fine particles, said particles being suspended in a cyanoacrylate ester which is capable of polymerizing upon coming into contact with moisture or skin tissue, said drug or therapeutic agent being a member selected from the group consisting of antibiotics, antivirals, antifungals, antibacterials, analgesics and antiseptics, said carbohydrate is a monosaccharide or a disaccharide, and said cyanoacrylate ester has the formula:

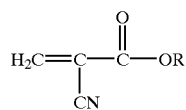

(Formula I)

wherein R is an alkyl of 2–12 C atoms, an alkenyl of 5–10 C atoms, phenyl, substituted phenyl, 2-ethoxyethyl, and 3-methoxybutyl.

18. The system of claim 17 wherein said particles have a diameter of from about 5 to about 50 millimicrons.

19. The system of claim 18 wherein said particles have a diameter of from about 10 to about 40 millimicrons.

20. The system of claim 17 wherein said monosaccharide is a member of the group consisting of glucose, mannose, galactose and fructose and said disaccharide is a member of the group consisting of sucrose, lactose, maltose and cellabiose.

21. The system of claim 17 wherein R is a linear or branched alkyl of 2–10 C atoms and cyclic isomers thereof.

22. The system of claim 17 wherein said drug or therapeutic agent is present in an amount of from about 5 to about 25% by weight of said carbohydrate and the weight ratio of said carbohydrate-encapsulated drug or therapeutic agent to said cyanoacrylate ester is about 1:5.

23. The system of claim 22 wherein said drug or therapeutic agent is present in an amount of from about 10 to about 20% by weight of said carbohydrate and the weight ratio of said carbohydrate-encapsulated drug or therapeutic agent to said cyanoacrylate ester is about 1:2.

24. The system of claim 17 which can optionally include a plasticizer or a polymerization inhibitor or both a plasticizer and a polymerization inhibitor.

25. The system of claim 24 wherein said plasticizer is dioctyl phthalate and is present in an amount of from about 5 to about 20% by weight and said polymerization inhibitor is sulfur dioxide and is present in an amount of from about 20 to about 400 ppm.

26. The system of claim 25 wherein said plasticizer is present in an amount of from about 10 to about 15% by weight and said polymerization inhibitor is present in an amount of from about 50 to about 300 ppm.

27. A transdermal drug delivery system comprising:

a drug or therapeutic agent encapsulated in a water soluble carbohydrate, said carbohydrate-encapsulated drug or therapeutic agent being in the form of finely divided micro-fine particles having a diameter of from about 5 to about 50 millimicrons, said particles being suspended in a cyanoacrylate ester which is capable of polymerizing upon coming into contact with moisture or skin tissue, said drug or therapeutic agent being a member selected from the group consisting of antibiotics, antivirals, antifungals antibacterials, analgesics and antiseptics, said carbohydrate is a monosaccharide selected from the group consisting of glucose, mannose, galactose and fructose or a disaccharide selected from the group consisting of sucrose, lactose, maltose and cellobiose, and said cyanoacrylate ester has the formula:

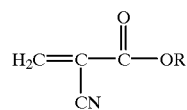

(Formula I)

wherein R is an alkyl of 2–12 C atoms, an alkenyl of 5–10 C atoms, phenyl, substituted phenyl, 2-ethoxyethyl and 3-methoxybutyl, said drug or therapeutic agent being present in an amount of from about 5 to about 25% by weight of said carbohydrate and the weight ratio of said carbohydrate-encapsulated drug or therapeutic agent to said cyanoacrylate ester being about 1:5, said system optionally including a plasticizer or a polymerization inhibitor or both a plasticizer and a polymerization inhibitor.

28. The system of claim 27 wherein said particles have a diameter of from about 10 to about 40 millimicrons.

29. The system of claim 27 wherein R is a linear or branched alkyl of 2–10 C atoms and cyclic isomers thereof.

30. The system of claim 27 wherein said drug or therapeutic agent is present in an amount of from about 10 to about 20% by weight of said carbohydrate and the weight ratio of said carbohydrate-encapsulated drug or therapeutic agent to said cyanoacrylate ester is about 1:2.

31. The system of claim 27 wherein said plasticizer is dioctyl phthalate and is present in an amount of from about 5 to about 20% by weight and said polymerization inhibitor is sulfur dioxide and is present in an amount of from about 20 to about 400 ppm.

32. The system of claim 3 wherein said plasticizer is present in an amount of from about 10 to about 15% by weight and said polymerization inhibitor is present in an amount of from about 50 to about 300 ppm.

33. A method for preparing a transdermal drug delivery system comprising:
  a) dissolving or suspending a drug or therapeutic agent in a molten, water soluble carbohydrate;
  b) cooling said molten carbohydrate to form a glass-like matrix in which said drug or therapeutic agent is encapsulated;
  c) pulverizing said glass-like matrix to obtain finely divided micro-fine particles having a diameter of from about 10 to about 400 millimicrons; and,
  d) suspending said particles in a cyanoacrylate ester capable of polymerizing upon coming into contact with moisture or skin tissue, said cyanoacrylate ester having the formula:

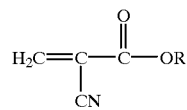

(Formula I)

wherein R is an alkyl of 2–12 C atoms, an alkenyl of 5–10 C atoms, phenyl, substituted phenyl, 2-ethoxyethyl and 3-methoxybutyl.

34. The method of claim 33 wherein said particles have a diameter of from about 10 to about 40 millimicrons.

35. The method of claim 33 wherein said carbohydrate is a monosaccharide or a disaccharide.

36. The method of claim 35 wherein said monosaccharide is a member of the group consisting of glucose, mannose, galactose and fructose and said disaccharide is a member of the group consisting of sucrose, lactose maltose and cellabiose.

37. The method of claim 33 wherein said drug or therapeutic agent is a member selected from the group consisting of antibiotics, antivirals, antifungals, antibacterials, analgesics and antiseptics.

38. The method of claim 33 wherein R is a linear or branched alkyl of 2–10 C atoms and cyclic isomers thereof.

39. The method of claim 33 wherein said drug or therapeutic agent is present in an amount of from about 5 to about 15% by weight of said carbohydrate and the weight ratio of said carbohydrate-encapsulated drug or therapeutic agent to said cyanoacrylate ester is about 1:5.

40. The method of claim 39 wherein said drug or therapeutic agent is present in an amount of from about 10 to about 20% by weight of said carbohydrate and the weight ratio of said carbohydrate-encapsulated drug or therapeutic agent to said cyanoacrylate ester is about 1:2.

41. The method of claim 33 wherein a plasticizer or a polymerization inhibitor or both a plasticizer and a polymerization inhibitor can optionally be added to said cyanoacrylate ester.

42. The method of claim 41 wherein said plasticizer is dioctyl phthalate and is present in an amount of from about 5 to about 20% by weight and said polymerization inhibitor is sulfur dioxide and is present in an amount of from about 20 to about 400 ppm.

43. The method of claim 42 wherein said plasticizer is present in an amount of from about 10 to about 15% by weight and said polymerization inhibitor is present in an amount of from about 50 to about 300 ppm.

* * * * *